(12) United States Patent
Mulrooney

(10) Patent No.: US 10,743,810 B2
(45) Date of Patent: Aug. 18, 2020

(54) DEVICES FOR AND METHODS OF DIAGNOSIS AND/OR MONITORING DYSPHAGIA

(71) Applicant: Phagenesis Limited, Manchester Greater Manchester (GB)

(72) Inventor: Conor Mulrooney, Manchester (GB)

(73) Assignee: Phagenesis Limited, Manchester (GB)

( * ) Notice: Subject to any disclaimer, the term of this patent is extended or adjusted under 35 U.S.C. 154(b) by 299 days.

(21) Appl. No.: 15/750,686

(22) PCT Filed: Aug. 4, 2016

(86) PCT No.: PCT/GB2016/052389
§ 371 (c)(1),
(2) Date: Feb. 6, 2018

(87) PCT Pub. No.: WO2017/025720
PCT Pub. Date: Feb. 16, 2017

(65) Prior Publication Data
US 2018/0235533 A1 Aug. 23, 2018

(30) Foreign Application Priority Data

Aug. 7, 2015 (GB) .................................. 1513989.2
Dec. 7, 2015 (GB) .................................. 1521538.7

(51) Int. Cl.
*A61B 5/00* (2006.01)
*A61N 1/05* (2006.01)
(Continued)

(52) U.S. Cl.
CPC .......... *A61B 5/4205* (2013.01); *A61B 5/6852* (2013.01); *A61J 15/0003* (2013.01);
(Continued)

(58) Field of Classification Search
CPC .. A61B 5/4205; A61B 5/6852; A61J 15/0003; A61J 15/0084; A61N 1/0517; A61N 1/36014
See application file for complete search history.

(56) References Cited

U.S. PATENT DOCUMENTS 6,366,813 B1 * 4/2002 DiLorenzo ............. A61B 5/048
607/45
7,324,851 B1 * 1/2008 DiLorenzo ........... A61N 1/3605
607/45
(Continued)

FOREIGN PATENT DOCUMENTS

CN 2033089196 U 1/2014
CN 203954394 U 11/2014
(Continued)

OTHER PUBLICATIONS

Great Britain Search Report for GB Application No. 1521538.7, dated Mar. 29, 2016, 4 pages.
(Continued)

*Primary Examiner* — Max F Hindenburg
(74) *Attorney, Agent, or Firm* — Maine Cernota & Rardin

(57) ABSTRACT

The use of a device to measure patient sensory response through the application of an incrementally increased electrical current to the oropharynx.

4 Claims, 3 Drawing Sheets

(51) Int. Cl.
*A61N 1/36* (2006.01)
*A61J 15/00* (2006.01)

(52) U.S. Cl.
CPC ........ *A61J 15/0084* (2015.05); *A61N 1/0517* (2013.01); *A61N 1/36014* (2013.01)

(56) References Cited

U.S. PATENT DOCUMENTS

| | | |
|---|---|---|
| 2010/0115739 A1 | 5/2010 | Mathur |
| 2010/0170066 A1 | 7/2010 | Honeycutt |
| 2011/0210215 A1 | 9/2011 | Nitsche et al. |
| 2013/0197321 A1 | 8/2013 | Wilson |
| 2013/0282078 A1* | 10/2013 | Wacnik ............ A61N 1/36071 607/59 |
| 2014/0378941 A1* | 12/2014 | Su ................ A61B 5/4255 604/506 |

FOREIGN PATENT DOCUMENTS

| | | |
|---|---|---|
| CN | 204319485 U | 5/2015 |
| EP | 11779307 A2 | 2/2013 |
| EP | 2693968 A1 | 2/2014 |
| JP | 2014068716 A | 4/2014 |
| WO | 2006024825 A1 | 3/2006 |
| WO | 2012131303 A1 | 10/2012 |

OTHER PUBLICATIONS

PCT Search Report and Written Opinion of PCT Application No. PCT/GB2016/052389, dated Nov. 2, 2016, 17 pages.
International Search Report for Appl No. GB1513792.0 dated Jan. 4, 2016, 4 pages.
International Search Report for Appl No. GB1521538.7 dated Mar. 29, 2016, 5 pages.
International Search Report for Appl No. GB1513797.9 dated Jan. 19, 2016, 3 pages.

* cited by examiner

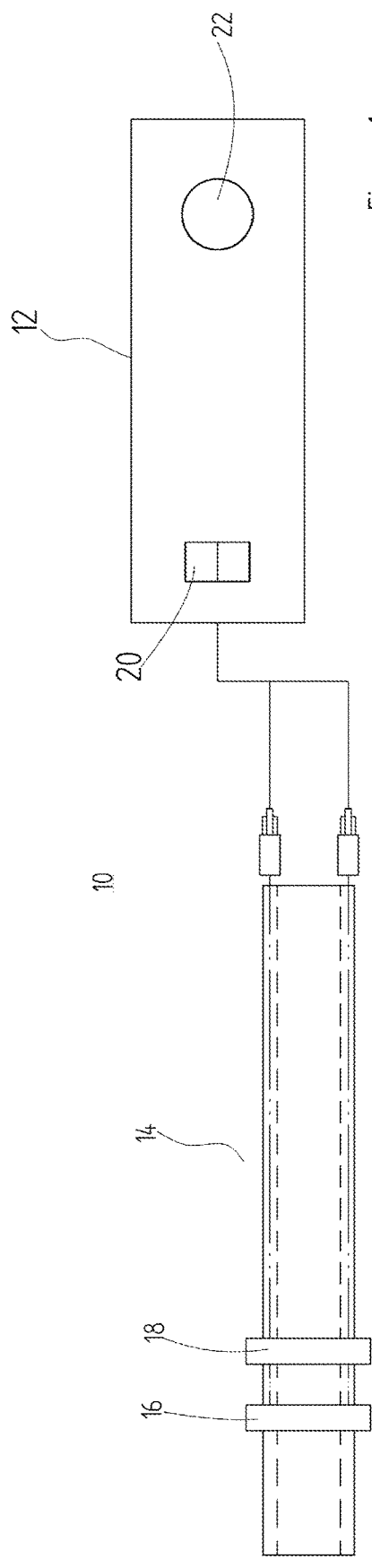
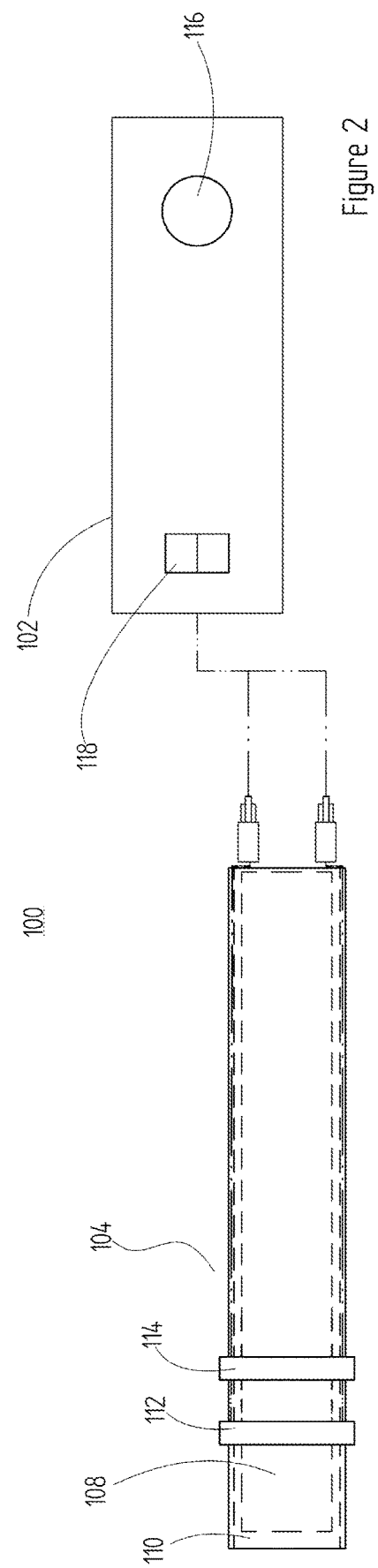

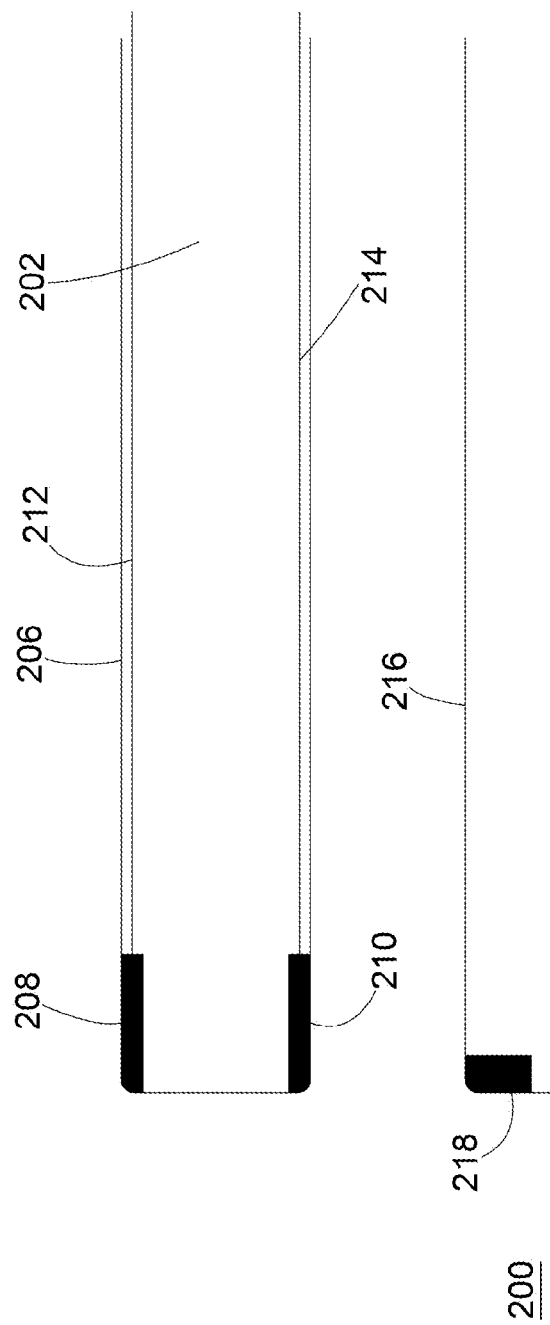
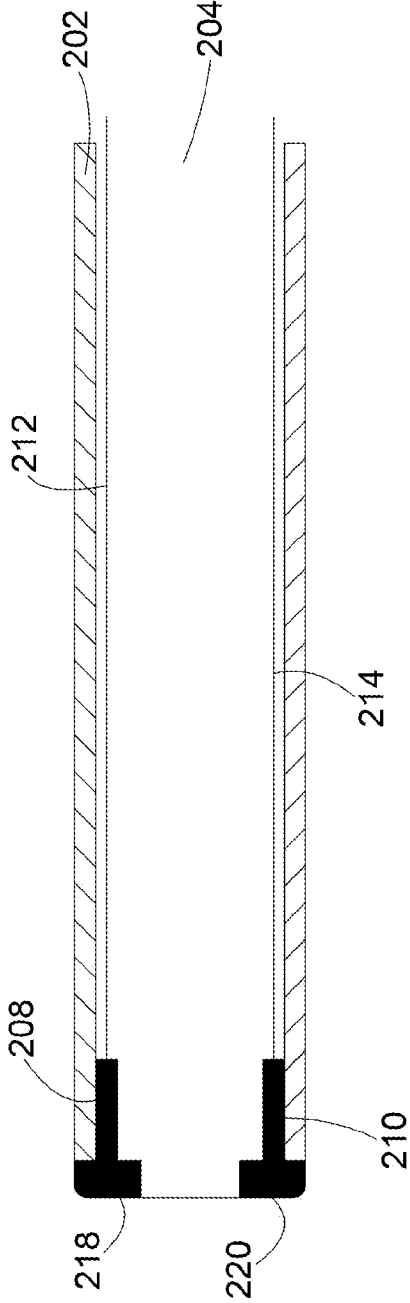

DEVICES FOR AND METHODS OF DIAGNOSIS AND/OR MONITORING DYSPHAGIA

RELATED APPLICATIONS

This application is a national phase application filed under 35 USC § 371 of PCT Application No. PCT/GB2016/052389 with an International filing date of Aug. 4, 2016, which claims priority of GB Patent Application GB 1513989.2, filed Aug. 7, 2015, and GB 1521538.7, filed Dec. 7, 2015. Each of these applications is herein incorporated by reference in its entirety for all purposes.

FIELD

The present invention relates to devices for and methods of diagnosis and/or monitoring dysphagia.

BACKGROUND

Dysphagia is a medical term given to an inability to swallow or an inability to swallow in a safely controlled way. It has been reported that 7%-10% of all adults older than 50 years of age present with clinically significant dysphagia. Of those over the age of 60, this increases to 14% of the entire adult population. In total 10 million Americans are evaluated each year in clinics and hospitals for swallowing difficulties. It has also been reported that >51% of institutionalised elderly patients present with oropharyngeal dysphagia.

Collectively these figures reflect the fact that neurogenic dysphagia (dysphagia arising from neurological damage) can develop due to a very wide range of underlying conditions such as traumatic brain injury, cerebral palsy, head and neck cancer and neurodegenerative diseases like MS, Parkinson's and Alzheimer's. It is however stroke that is probably the most recognized single cause of dysphagia—greater than 50% of patients who have a stroke will present with dysphagia.

Complications that have been associated with dysphagia post-stroke include pneumonia, malnutrition, dehydration, poorer long-term outcome, increased length of hospital stay, increased rehabilitation time and the need for long-term care assistance, increased mortality, and increased health care costs. These complications impact the physical and social well being of patients, quality of life of both patients and caregivers, and the utilization of health care resources.

Dysphagia can be difficult to diagnose and to monitor. Symptoms may improve or worsen over even short periods of time. Gold standard diagnostic methods for swallowing assessment involve the use of instrumental exams that visualise the movement of materials from the oral spaces to the oesophagus. Examples of such methods include videofluoroscopy (VFS) and Fibroscopic Endoscopic Evaluation of Swallowing (FEES). These allow quantification of the time involved in the movement of a bolus of material through the oral spaces, the amount of swallowed material that pools in the pharynx and the amount of material that enters into the airways. They can also capture the response of the patient to material entering into the airways as a determinant of level of awareness the patient has to this risk associated event and their ability to respond to it. These methods can be difficult or traumatic for the patient and require substantial expertise and training.

Other diagnostic methods include bedside assessments such as the Toronto Bedside Swallow Test (TORBST). These are observational methods that test the ability of the subject to swallow a variety of different materials. These methods are more qualitative in nature and are designed to screen for the presence or absence of a normal swallow. Whilst they have the advantage of being easy to carry out they lack the diagnostic sensitivity of instrumental methods and in particular are poor at identifying so called silent aspirators whose sensory processes are so compromised they do not react to even substantial amounts of material entering the airways.

The pharyngeal phase of swallowing is initiated voluntarily. This first requires input and oversight from the parts of the brain involved in motor planning. These higher centres receive information about the nature of the material, size of the bolus etc., and modulate the involuntary sequences that will follow. The duration and intensity of muscle contraction can be modified to accommodate a larger bolus for example. Only when the food or liquid bolus is voluntarily pushed through the faucial pillars (the structures to the left and right of the uvula), or in older individuals, when the food is in contact with the base of the tongue, is the reflexive involuntary component of the pharyngeal swallow triggered. This is where the central pattern generator within the medulla (brain stem), modulated by the higher centres comes into play. The reflexive sequence that follows has two key functions: i) controlled passage of food or secretions from the pharynx to the oesophagus; and ii) airway protection.

A common manifestation in neurogenic dysphagia is that whilst the pattern generating processes that control the sequence of activities in swallowing (located in the brain stem) may be intact, the triggers to begin or modulate the swallowing processes are absent or compromised. This can reflect the fact that the sensory input provided by the bolus of material at the back of the throat or base of the tongue is no longer sufficient to be detected and to trigger the reflexive swallowing process. In effect the sensory threshold for that individual has been raised. Whilst the consequences of this increase in sensory threshold may be seen with existing diagnostic methods, the increase and absolute level of the threshold is not measured by these methods.

Pharyngeal Electrical Stimulation (PES) is a method for treating neurogenic dysphagia. It involves the application of electrical stimulation to the pharyngeal mucosa and this results in an increase in activity in the motor cortex and other areas of the brain. These changes facilitate a functional reorganisation of the centres in the brain responsible for controlling and coordinating swallow function.

SUMMARY OF THE INVENTION

As used herein, the term patient sensory response data shall be interpreted as meaning the patient's sensory threshold, i.e. the weakest electrical current that a patient can detect.

As used herein, the term control sensory response data shall be interpreted as meaning either: i) a sensory response range as would be expected from a healthy individual who is not suffering from dysphagia, ii) a sensory response range as would be expected from an individual suffering from dysphagia or ii) at least one previous patient sensory response data entry obtained from a specific patient and in the case of multiple data entries obtained from a patient over time, said data entries are plotted on a curve to indicate the extent and speed of recovery from dysphagia by comparing the slope of the curve with other control sensory response data obtained from other patients who exhibited recovery from dysphagia.

An aspect of the present invention provides a device for diagnosing dysphagia, the device comprising: a catheter for oral or nasal insertion into a patient, the catheter comprising an elongate body having at least one electrode mounted on or about the elongate body, said at least one electrode configured to receive a variable electrical current for applying electrical stimulation to the patient's oropharynx, and a control unit comprising an electrical current generator, a non-volatile memory for storing patient sensory response data and control sensory response data, means for recording the patient's sensory response to the applied electrical stimulation and a processor for comparing the patient's sensory response to a control sensory response and determining whether the patient is suffering from dysphagia and/or monitoring the patient's recovery from dysphagia.

Another aspect of the present invention provides a device for diagnosing and/or treating dysphagia, the device comprising: a control unit, and a catheter for oral or nasal insertion into a patient, and wherein the catheter comprises a nasal gastrointestinal feeding tube and a sleeve selectively movable relative to the feeding tube, the sleeve having at least one electrode mounted thereon, said at least one electrode configured to receive a variable electrical current for applying electrical stimulation to the patient's oropharynx, and a control unit comprising an electrical current generator, a non-volatile memory for storing patient sensory response data and control sensory response data, means for recording the patient's sensory response to the applied electrical stimulation and a processor for comparing the patient's sensory response to a control sensory response and determining whether the patient is suffering from dysphagia and/or monitoring the patient's recovery from dysphagia.

Another aspect of the present invention provides a method of diagnosing dysphagia, the method comprising: i) applying an electrical current of between 1 mA and 50 mA to a patient's oropharynx; ii) increasing the current incrementally; iii) obtaining patient sensory feedback after each incremental increase in current; iv) comparing the patient's sensory response with a control sensory response; and v) determining whether the patient is suffering from dysphagia and/or monitoring the patient's recovery from dysphagia.

Devices and methods of the present invention enable a medical professional to make a diagnosis of dysphagia and/or monitor a patient's recovery from dysphagia. Over time, patient's suffering from dysphagia may show signs of clinical improvement whether as a result of treatment, such as pharyngeal electrical stimulation, or through spontaneous recovery. The applicant has observed that an improvement in swallowing ability, i.e. an improvement in the patient's clinical condition, broadly corresponds to a reduction in the patient's sensory response, i.e. the patient's sensory threshold is lower. During treatment a patient would be expected to exhibit a reducing sensory threshold and this trend would be indicative of a corresponding improvement in swallowing function. The same trend would be observable in patient's who have not received treatment but whose clinical condition has spontaneously improved.

FIGURES

Aspects of the invention will now be described by way of reference to the following figures:

FIG. 1 shows a first embodiment of a device according to the present invention;

FIG. 2 shows a second embodiment of a device according to the present invention;

Figure 4:
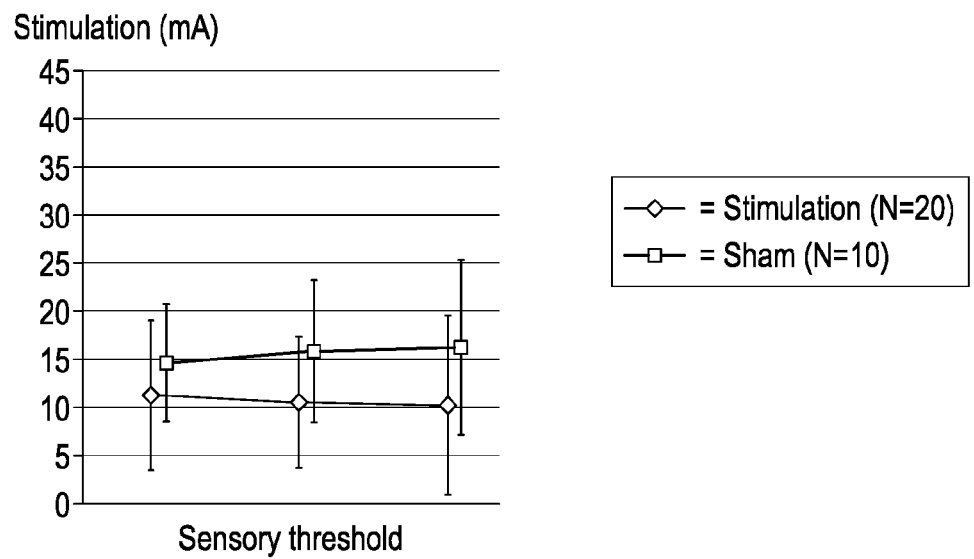

FIGS. 3*a*, 3*b* and 3*c* show a third embodiment of a device according to the present invention;

FIG. 4 shows sensory threshold levels in treated and untreated subjects over three consecutive days whereby the treated group also improved their swallow function;

DESCRIPTION

FIG. 1 shows a device (10) for diagnosing dysphagia. The device (10) comprises a control unit (12) and a catheter (14). The control unit (12) comprises a variable electric current generating means for delivering electrical current to the catheter (14). The control unit (12) further comprises a non-volatile memory for storing patient sensory response data and/or control sensory response data and a processing means for comparing and/or processing patient sensory response data against said control sensory response data to make a diagnostic determination of whether a patient is suffering from dysphagia and/or monitoring the patient's recovery from dysphagia.

The catheter (14) has a at least one electrode (16,18) mounted thereon. The at least one electrode (16,18) is electrically connected to the variable electric current generating means of the control unit (12). The catheter (14) may be single use or re-usable.

In embodiments of the invention described with reference to FIG. 1, the device (10) may be configured to provide Pharyngeal Electrical Stimulation (PES) and to provide a recommendation for further treatment based on patient sensory response.

FIG. 2 shows a device (100) for diagnosing dysphagia and for providing nutrition. The device (100) comprises a control unit (102) and a catheter (104). The control unit (102) comprises a variable electric current generating means for delivering electrical current to the catheter (104). The control unit (102) further comprises a non-volatile memory for storing patient sensory response data and/or control sensory response data and a processing means for comparing and/or processing patient sensory response data against control sensory response data to make a diagnostic determination of whether a patient is suffering from dysphagia and/or to monitor the patient's recovery from dysphagia.

The catheter (104) comprises a NG feeding tube (108) and a sleeve (110) selectively movable relative to the NG feeding tube (108). The sleeve (110) carries at least one electrode (112, 114) and wiring connecting the at least one electrode (112, 114) to the control unit (102).

Each of the devices (10, 100) of FIGS. 1 and 2 are either provided with a rechargeable battery (not shown) or are electrically connectable to a power source, or both. Each device (10, 100) is also provided with a power selector (20, 118) to turn the device (10, 100) on/off and a control means (22, 116) to select the level of current to be delivered to the at least one electrode (18, 112). In some embodiments a graphical display is provided to visually identify to a medical professional that a patient is suffering from dysphagia and/or to indicate a change in the patient's clinical condition. In other embodiments a speaker is provided to audibly identify to a medical professional that a patient is suffering from dysphagia and/or to indicate a change in the patient's clinical condition. In other embodiments the device (10, 100) is equipped with wireless communications technology to transmit information relating to diagnosis and treatment to a server, network or independent device such as smartphone, tablet or laptop. The wireless communications technology could be WIFI, Bluetooth or GSM, for example, but is not limited thereto.

Each device (10, 100) has a diagnostic mode for diagnosing whether a patient is suffering from dysphagia and/or for monitoring a change in the patient's clinical condition. The control unit (12, 102) collects patient sensory response data and stores said data against a specific patient record in the non-volatile memory of the device (10, 100). The control unit (12, 102) can therefore compare instantaneous patient sensory response data against control sensory response data to monitor a patient's response to PES over time to determine whether or not further PES is required.

The device (10, 100) is turned on by activation of the power selector (20, 116). The control means (22, 116) is used to select the current level and is typically set to a current level that is not detectable by a patient, i.e. 1 mA. The catheter is inserted orally or nasally into the patient and the at least one electrode (16, 18, 112, 114) is aligned with the patient's oropharynx.

The control means (22, 116) is used to activate the at least one electrode (14, 112) and impart the 1 mA electrical current into the patient's tissue. The control means (22, 116) is then used to increase the electrical current in 1 mA increments up to a maximum of 50 mA. After each increment the patient will be requested to confirm whether they can sense the electric current or not. If the patient cannot sense the electric current it will be increased by a further 1 mA. If the patient can sense the electric current the current level will be recorded as patient sensory response data.

When using the device (10, 100), the patient sensory data will be saved in the non-volatile memory against that individual patient's record. In certain embodiments the non-volatile memory is integral to the device (10, 100) and data contained therein is uploaded to a remote server either wirelessly or by plugging the device (10, 100) into a separate device connected to a server. Such a device (10, 100) can also store patient data uploaded thereto from a server or other device. Such data can be used by the device (10, 100) to compare patient sensory response data against control sensory response data. Such comparison is used by the device (10, 100) to diagnose dysphagia by comparing patient sensory response data to control sensory response data. The device (10,100) can be used to monitor unassisted recovery from dysphagia and recovery as a result of PES.

FIG. 3 shows a device (200) for applying electrical stimulation to a patient's oropharynx. The device (200) comprises a re-usable probe (202), as detailed in FIG. 3a, and a disposable sleeve (204), as detailed in FIG. 3b. The re-usable probe (202) comprises a tubular body (206), which may be rigid, semi-rigid or flexible, and a pair of terminally located electrodes (208, 210). Conducting wires (212, 214) are connected between each electrode (208, 210) and an electrical current generator (not shown).

The disposable sleeve (204) comprises a hollow tubular body (216) closed at one end. The closed end of the tubular body includes one or more areas (218, 220) that are capable of conducting an electric current from the electrodes (208, 210) through the sheath in the direction of the longitudinal axis of the device (200).

In use, as shown in FIG. 3c, the probe (202) is inserted into the sleeve (204) so that the pair of electrodes (208, 210) are aligned and substantially in contact with the one or more conductive areas (218, 220) of the sleeve (204).

Studies

Studies were conducted in two patient groups; a treatment arm and a control arm. Each patient in the treatment arm received a stimulation level that is specifically tailored to their treatment needs. This level is determined through first establishing their sensory threshold and thereafter their tolerance level (the highest level of applied stimulation the patient can tolerate for the treatment period). A suitable stimulation level is then derived from these two parameters.

A randomised controlled trial of PES in the control arm consisting of 30 subjects with dysphagia and a tracheotomy was performed to assess whether treatment resulted in sufficient restoration of safe swallowing to allow the tracheotomy cannula to be removed. As part of this study the threshold and tolerance levels of subjects in both the treatment and control arms were recorded.

FIG. 4 shows the initial and subsequent mean threshold levels for the treatment (Stimulation) arm and the control (Sham) arms. It can be seen that whilst the initial sensory threshold levels were similar, over the course of treatment the sensory threshold levels in the group receiving stimulation decreased whilst those not receiving stimulation actually increased.

This data suggests that decreasing sensory threshold levels are linked to swallowing recovery and that the trend in sensory level over time may also be indicative of the extent to which the subject is responding to treatment.

The invention claimed is:

1. A device for determining whether a patient is suffering from dysphagia, the device comprising:
   a catheter for oral or nasal insertion into a patient, the catheter comprising an elongate body having at least one electrode mounted on or about the elongate body, said at least one electrode configured to receive a variable electrical current for applying electrical stimulation to the patient's oropharynx, and
   a control unit comprising an electrical current generator, a non-volatile memory for storing patient sensory response data and control sensory response data, a recorder configured to record the patient's sensory response to the applied electrical stimulation and a processor for comparing the patient's sensory response to a control sensory response stored in the non-volatile memory and determining whether the patient is suffering from dysphagia.

2. The device for determining whether a patient is suffering from dysphagia of claim 1 wherein said catheter for oral or nasal insertion into a patient comprises a nasal gastrointestinal feeding tube and wherein said at least one electrode is disposed on a sleeve selectively movable relative to the feeding tube.

3. A device for monitoring a patient's recovery from dysphagia, the device comprising:
   a catheter for oral or nasal insertion into a patient, the catheter comprising an elongate body having at least one electrode mounted on or about the elongate body, said at least one electrode configured to receive a variable electrical current for applying electrical stimulation to the patient's oropharynx, and
   a control unit comprising an electrical current generator, a non-volatile memory for storing patient sensory response data and control sensory response data, a recorder configured to record the patient's sensory response to the applied electrical stimulation and a processor for comparing the patient's sensory response to a control sensory response stored in the non-volatile memory and monitoring a patient's recovery from dysphagia.

4. The device for determining whether a patient is suffering from dysphagia of claim 1 wherein said catheter for oral or nasal insertion into a patient comprises a nasal gastrointestinal feeding tube and wherein said at least one electrode is disposed on a sleeve selectively movable relative to the feeding tube.

\* \* \* \* \*